United States Patent
May et al.

(10) Patent No.: US 6,806,285 B1
(45) Date of Patent: Oct. 19, 2004

(54) 5-HYDROXYL INDOLE DERIVATIVES FOR TREATING GLAUCOMA

(75) Inventors: Jesse A. May, Fort Worth, TX (US); Paul W. Zinke, Fort Worth, TX (US)

(73) Assignee: Alcon, Inc., Hunenberg (CH)

(*) Notice: Subject to any disclaimer, the term of this patent is extended or adjusted under 35 U.S.C. 154(b) by 0 days.

(21) Appl. No.: 10/220,997

(22) PCT Filed: Nov. 14, 2000

(86) PCT No.: PCT/US00/31144

§ 371 (c)(1), (2), (4) Date: Sep. 5, 2002

(87) PCT Pub. No.: WO01/70686

PCT Pub. Date: Sep. 27, 2001

Related U.S. Application Data

(60) Provisional application No. 60/190,205, filed on Mar. 17, 2000.

(51) Int. Cl.[7] ......................... A61K 31/40; C07D 209/44
(52) U.S. Cl. ........................................ 514/416; 548/470
(58) Field of Search ........................... 548/470; 514/416

(56) References Cited

U.S. PATENT DOCUMENTS

| | | |
|---|---|---|
| 3,732,245 A | 5/1973 | Batcho et al. |
| 4,690,931 A | 9/1987 | Wick et al. |
| 5,151,444 A | 9/1992 | Ueno et al. |
| 5,296,504 A | 3/1994 | Stjernschantz et al. |
| 5,352,708 A | 10/1994 | Woodward et al. |
| 5,422,368 A | 6/1995 | Stjernschantz et al. |
| 5,494,928 A | 2/1996 | Bös |
| 5,571,833 A | 11/1996 | Kruse et al. |
| 5,874,477 A | 2/1999 | McConnell et al. |
| 5,889,052 A | 3/1999 | Klimko et al. |
| 5,902,815 A | 5/1999 | Olney et al. |

FOREIGN PATENT DOCUMENTS

| | | |
|---|---|---|
| WO | WO 93/00333 A1 | 1/1993 |
| WO | WO 94/03162 A1 | 2/1994 |
| WO | WO 94/13275 | 6/1994 |
| WO | WO 98/31354 A2 A3 | 7/1998 |
| WO | WO 00/12475 | 3/2000 |
| WO | WO 00/16761 A2 A3 | 3/2000 |
| WO | WO 00/35922 | 6/2000 |

OTHER PUBLICATIONS

Bodor, Nicholas, et al., "Improved Delivery Through Biological Membranes, XVII3. A Site–Specific Chemical Delivery System as a Short–Acting Mydriatic Agent", Pharm. Res., 168–173 (1984).

Chemical Abstract, Lyon, Robert A, et al., "Indolealkytamine analogs share 5–HT2 binding characteristics with phenylalkylamine hallucinogens", Database accession No. 109:47843 [XP002161467] abstract; Eur. J. Pharmacol., 45(3), 291 1988 (Chem. Abs.) [D8].

Fiorella, et al., "Role of 5–HT2A and 5–HT2C receptors in the stimulus effects of hallucinogenic, drugs II: reassessment of LSD false positives", Psychopharmacology, 121:357 (1995).

Flaugh, M. E., et al., "Synthesis and Evaluation of the Antiovulatory Activity of a Variety of Melatonin Analogues", Journal of Medicinal Chemistry, 22:63–69 (1979).

Gupta, Y.K., et al., "Therapeutic Potentials Of 5–HT Receptor Modulators", Indian Journal of Pharmacology, vol. 26, No. 2, pp. 94–107 (Jun. 1, 1994) [XP000571272] [D5].

Heinzelman, R.V., et al., "The Synthesis of a–Methyltryptophans and a–Alkytryptamines", J. Org. Chem, 25,:1548–1558 (1960).

Ismaiel, Abd M., et al., "5–HT1 and 5–HT2 Binding Profiles of the Serotonergic Agents.Alpha.–Methylserotonin and 2–Methylserotonin", Journal Med. Chem., vol. 33, No. 2, pp. 755–758 (1990) [XP000876594] [D7].

Osborne, N. N., "Serotonin and melatonin in the Iris/ciliary processes and their Involvement in intraocular pressure", ACTA Neurobiologiae Experimentalis, vol. 54 (Suppl.), pp. 57–64 (1994) [XP000878634] [D6].

Osborne, N. N., et al., "Do Beta–Andrenoceptors and Serotonin 5–HT1A Receptors Have Similar Functions in the Control of Intraocular Pressure in the Rabbit?", Opthalmologica, CH, Karger, Basel, vol. 210, pp. 308–314 (1996) [XP002051581] [D4].

Wrona, M. Z. and Dryhurst, Glenn, "Further Insights into the Oxidation Chemistry of 5–Hydroxytryptamine", Journal of Pharmaceutical Sciences, 77:911–917 (1988).

Wrona, M, Z. and Dryhurst, G., "Oxidation Chemistry of 5–Hydroxytryptamine. 1, Mechanism and Products Formed at Micromolar Concentrations" J. Org. Chem, 52:2817–2825 (1987).

*Primary Examiner*—Johann Richter
*Assistant Examiner*—Ebenezer Sackey
(74) *Attorney, Agent, or Firm*—Barry L. Copeland

(57) ABSTRACT

Novel 3-(2-aminopropyl)-H-indol-5-ols useful for lowering and controlling IOP and treating glaucoma are disclosed.

5 Claims, No Drawings

5-HYDROXYL INDOLE DERIVATIVES FOR TREATING GLAUCOMA

This application claims priority from PCT/US00/31144 filed on Nov. 14, 2000, and U.S. Ser. No. 60/190,205, filed on Mar. 17, 2000.

The present invention is directed to novel substituted 3-(2-aminopropyl)-1H-indol-5-ols. These novel compounds are useful for lowering and controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are is considered to be a high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

It has been found that serotonergic compounds which possess agonist activity at 5-$HT_2$ receptors effectively lower and control normal and elevated IOP and are useful for treating glaucoma, see commonly owned co-pending application, PCT/US99/19888. Compounds that act as agonists at 5-$HT_2$ receptors are known and have shown a variety of utilities, primarily for disorders or conditions associated with the central nervous system (CNS). U.S. Pat. No. 5,494,928 discloses certain 2-(indol-1-yl)-ethylamnine derivatives that are 5-$HT_{2c}$ agonists for the treatment of obsessive compulsive disorder and other CNS derived personality disorders. U.S. Pat. No. 5,571,833 discloses typtamine derivatives that are 5-$HT_2$ agonist for the treatment of portal hypertension and migraine. U.S. Pat. No. 5,874,477 discloses a method for treating malaria using 5-$HT_{2A/2C}$ agonists. U.S. Pat. No. 5,902,815 discloses the use of 5-$HT_{2A}$ agonists to prevent adverse effects of NMDA receptor hypo-function. WO 98/31354A2 discloses 5-$HT_{2B}$ agonists for the treatment of depression and other CNS conditions. WO 00/12475 discloses indoline derivatives as 5-$HT_{2B}$ and 5-$HT_{2C}$ receptor agonists for the treatment of a variety of disorders of the central nervous system, but especially for the treatment of obesity. WO00/35922 discloses certain pyrazino[1,2-a]quinoxaline derivates as 5-$HT_{2C}$ agonists for the treatment of obsessive-compulsive disorder, depression, eating disorders, and other disorders involving the CNS. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

A specific disclosure in co-pending application PCT/US99/19888 relates to certain substituted α-methyltryptamines which are effective agents for lowering intraocular pressure in mammals (Table 1). However, when a phenolic moiety is included in this substitution, e.g. a hydroxyl group at indole ring position five such compounds can be particularly sensitive to oxidation reactions well known to occur with phenolic compounds in general, including hydroxytryptamines [*J. Phys. Chem.* 103, 8606 (1999), *Chem. Res. Toxicol.* 11, 639 (1998), *J. Org. Chem.* 52, 2817 (1987), *J. Pharm. Sci.* 77, 911 (198 9)], which are of particular relevance to the present application. Protection of such hydroxy substituted tryptamines from oxidation can be accomplished by derivatization of the aryl hydroxy group to provide a suitable ester, carbamate, or carbonate. Though the ester, carbamate, or carbonate derivatives do not themselves possess a high affinity for the above mentioned receptors, they do have utility in the treatment of glaucoma since suitably protected phenols can be cleaved in vivo either by chemical hydrolysis or through the action of tissue esterases, thereby delivering the desired therapeutic agent, that is, the desired hydroxytryptamine compound in the present case. The concept of utilizing such derivatized phenolic compounds as chemical delivery agents is well known in the art [*Drugs Pharm. Sci.* 53, 221 (1992), *Pharm. Res.*, 168 (1984)].

TABLE 1

IOP Response in hypertensive cynomolgus monkeys.

| Example | Dose, μg | Baseline IOP (mmHg) | Percent IOP Reduction ± SEM Hours after dose | | |
|---|---|---|---|---|---|
| | | | 1 | 3 | 6 |
| α-Methyl-serotonin | 250 | 41.8 | 14.2 ± 4.39 | 25.8 ± 5.16 | 30.8 ± 7.72 |
| Serotonin | 250 | 33.5 | 13.3 ± 5.31 | 18.0 ± 5.12 | 2.0 ± 7.39 |

SUMMARY OF THE INVENTION

The present invention is directed to new derivatives of 3-(2-aminopropyl)-1H-indol-5-ol which can be used to lower and control IOP associated with normal-tension glaucoma, ocular hypertension, and glaucoma in warm blooded animals, including man. The compounds are formulated in pharmaceutical compositions suitable for topical delivery to the eye.

DESCRIPTION OF THE PREFERRED EMBODIMENTS

Compounds that are useful according to the present invention are represented by the following Formula I.

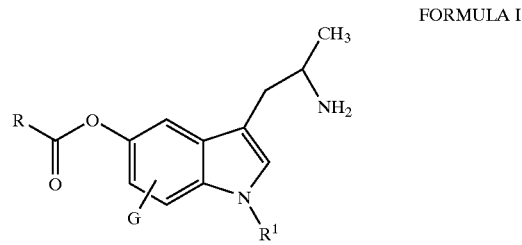

FORMULA I

Wherein G is chosen from hydrogen, halogen, or $C_{1-4}$ alkyl; R is chosen from $C_{3-6}$alkyl, $C_{3-6}$alkyl substituted with hydroxyl, $CO(OC_{1-4}alkyl)$, $CON(C_{1-4}alkyl)_2$, or $C_{2-4}$alkenyl substituted by phenyl;

$R^1$ is chosen from hydrogen, $C_{1-4}$alkyl; and pharmaceutically acceptable salts and solvates of the compounds.

It is recognized that compounds of Formula I can contain one or more chiral centers. This invention contemplates all enantiomers, diastereomers and mixtures thereof.

In the above definitions, the total number of carbon atoms in a substituent group is indicated by the Ci-j prefix where the numbers i and j define the number of carbon atoms; this definition includes branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Synthesis

The compounds of Formula I can be readily prepared from, for example. α-methyl-5-hydroxy-tryptamine [*J. Med. Chem.* 33, 755 (1990), *J. Org. Chem.* 25, 1548 (1960)] or a desirably substituted derivative of structure 1 wherein G is as defined previously. That is, compounds of Formula I can be prepared by reacting the appropriate indole 1, or preferably a suitable amino-protected intermediate, e.g. 2 (Scheme 1) with the desired activated acid derivative, such as an acid halide or active ester, or the like, to provide the esters 3. Removal of the N-protective group from the intermediate 3 provides the desired compounds of Formula I.

The indole derivatives of interest for use as starting materials for the preparation of 1 can be either purchased from commercial suppliers or prepared by well known methods [*comp. Heterocyl. Chem.* II, vol. 2:119, 1996; *Indoles*, Sundberg, 1996]. For example, one such approach begins with the desired 5-alkoxy-2-nitrotoluene 5 and proceeds via a Leimgruber-Batcho indole synthesis [*J. Med. Chem.* 22, 63 (1979) and U.S. Pat. No. 3,732,245] to give the desired indoles 7 (Scheme 2). Intermediates 7 can be readily transformed into indoles 1 by well known methods [*J. Med. Chem.* 33, 755 (1990), *J. Org. Chem.* 25, 1548 (1960)].

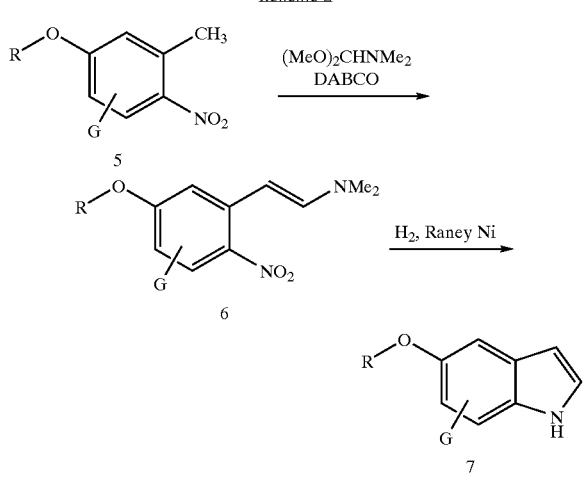

The compounds of this invention, Formula I, can be incorporated into various types of ophthalmic formulations for delivery to the eye (e.g. topically, intracamerally, or via an implant). The compounds are preferably incorporated into topical ophthalmic formulations for delivery to the eye. The compounds may be combined with ophthalmologically acceptable preservatives, surfactants viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as, hydroxymethylcellulose, hydroxyethylcellulose,

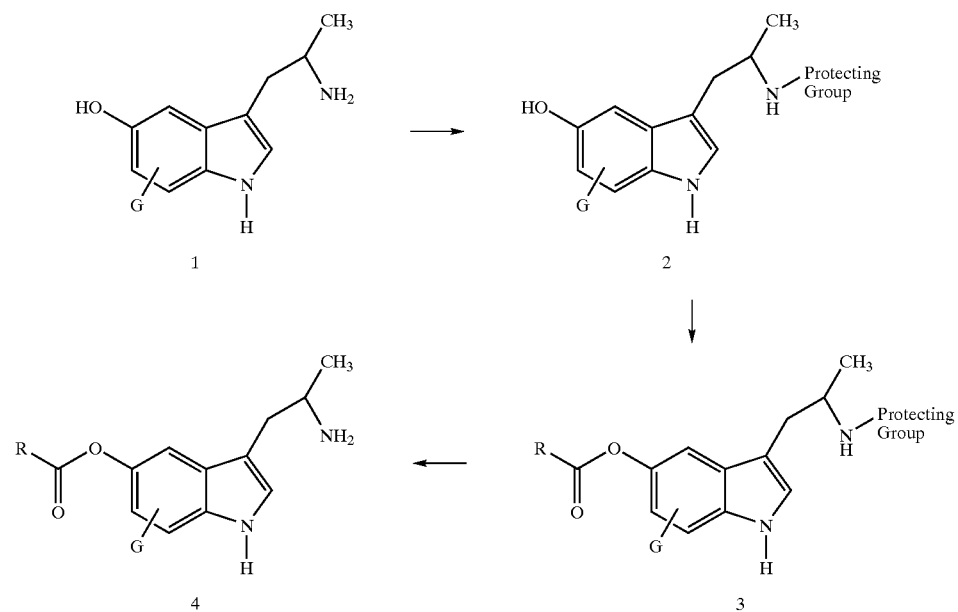

hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), α1 antagonists (e.g. nipradolol), α2 agonists (e.g., iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 06/203350, and appropriate compounds from WO94/13275, including memantine.

The following examples are given to illustrate the preparation of compounds that are the subject of this invention but should not be construed as implying any limitations to the claims. The preferred compounds of Formula I are described in Examples 2–4. Especially preferred compounds are those set forth in Examples 3 and 4. The most preferred is the compound of Example 3. The proton magnetic resonance spectrum of each compound of the Examples was consistent with the assigned structure. All compounds had satisfactory HPLC analysis.

EXAMPLE 1

Propionic acid 3-(2-aminopropyl)1H-indol-5-yl ester

Step A. [2-(5-Hydroxy-1H-indol-3-yl)-1-methylethyl] carbamic acid 9H-fluoren-9-ylmethyl ester A 35 mL round bottom flask was charged with 3-(2-aminopropyl)-1H-indol-5-ol (0.20 g, 0.65 mmol) was added $NaHCO_3$ (0.9 g, 11 mmol), water (2 mL) and 1,4-dioxane (8 mL). 9-Fluorenylmethyl chloroformate (0.20 g, 0.82 mmol) was added and the mixture stirred for 16 h at 23° C. TLC analysis indicated that the reaction was complete and the solution decanted into aqueous $NaHCO_3$, then extracted with ether (2×30 mL). The combined organic extracts were washed with water (20 mL), dried over $MgSO_4$ and concentrated. The crude product was purified by chromatography (silica, 65:35 hexanes:ethyl acetate) to furnish the title compound (0.26 g, 97%): $^1H$ NMR ($CDCl_3$) δ 7.88 (bs, 1H), 7.76 (d, J =6 Hz, 2H), 7.57 (d, J=6 Hz, 2H), 7.44–7.19 (m, 6H), 7.07 (s, 1H), 6.94 (s, 1H), 6.77 (dd, J=8, 2 Hz, 1H), 4.8 (m. 1H), 4.45 (m, J=8 Hz, 2H), 4.20 (m, J=8 Hz, 1H), 2.81 (bm, 2H), 1.15 (d, J=8 Hz); MS(ESI) m/z 430 $(M+NH_4)^+$, 413 $(M+H)^+$.

Step B. Propionic acid 3-[2-(9H-fluoren-9-ylmethoxycarbonylamino)propyl]-1H-indol-5-yl ester A 25 mL round bottom flask fitted with magnetic stirring bar and septum inlet was charged with the product from Step A (0.24 g, 0.58 mmol), $CH_2Cl_2$ (10 mL), and diisopropyl-ethyl amine (0.12 g, 0.9 mmol). Propionyl chloride (0.083 g, 0.9 mmol) was added followed by addition of DMAP (0.005g, 0.04 mmol). The solution was stirred for 14 h at 23° C., then poured into dilute aqueous $NaHCO_3$ and extracted with ether (2×20 mL). The combined extracts were dried ($MgSO_4$), filtered, and concentrated. The crude material was purified by chromatography (silica, 7:3 to hexanes:ethyl acetate) to furnish the title compound (0.15 g, 55%): $^1H$ NMR ($CDCl_3$) δ 8.03 (bs, 1H), 7.76 (d, J=6 Hz, 2H), 7.56 (d, J=6 Hz, 2H), 7.43–7.29 (m, 7H), 6.99 (bs, 1H), 6.77 (dd, J=8, 2 Hz, 1H), 4.43 (m, 1H), 4.37 (m, J=8 Hz, 2H), 4.20 (m, J=8 Hz, 1H), 2.84 (bm, 2H), 2.58 (q, J=6 Hz, 2H), 1.25 (q, J=6 Hz, 3H), 1.15 (d, J=8 Hz, 3H); MS(ESI) m/z 486 $(M+NH_4)^+$, 469 $(M+H)^+$.

Step C: Propionic acid 3-(2aminopropyl)-1H-indol-5-yl ester

A 10 mL round bottom flask fitted with magnetic stirring bar and septum inlet was charged with the product from Step B (0.14 g, 0.30 mmol), DMF (4 mL), and piperidine (1 mL, 0.9 mmol). The solution was stirred for 5 minutes, then poured into dilute aq. $NaHCO_3$ (1 mL) and extracted with ethyl acetate (3×10 mL), and $CH_2Cl_2$ (1×10 mL). The combined organic extracts were concentrated and the crude material purified by chromatography (silica, gradient, 10% to 50% MeOH in $CH_2Cl_2$) to provide the title compound (0.046 g, 63%): $^1H$ NMR ($CDCl_3$) δ 8.1 (bs, 1H), 7.31 (dd, J=8, 2 Hz, 1H), 7.2 (s, 1H), 6.92 (d, J=2 Hz, 1H), 6.85 (dd, J=8, 2 Hz, 1H), 3.2 (m, 1H), 2.9–2.4 (m, 4H), 1.29 (t, J=8 Hz, 3H), 1.17 (d, J=8 Hz 3H); MS(ESI) m/z 247 $(M+H)^+$.

EXAMPLE 2

Isobutyric acid 3-(2-aminopropyl)-1H-indol-5yl ester

Step A. Isobutyric acid 3-[2-(9H-fluoren-9-ylmethoxycarbonylamino)-propyl]-1H-indol-5-yl ester Prepared as described in Example 1, Step B but using isobutyryl chloride: oil. 83% yield; $^1H$ NMR ($CDCl_3$) δ 8.05 (bs, 1H), 7.75 (d, J=6 Hz, 2H), 7.54 (d, J=6Hz, 2H), 7.43–7.29 (m, 7H), 6.97 (bs, 1H), 6.87 (dd, J=8, 2 Hz, 1H), 4.43 (m,1H), 4.37 (m. J=8 Hz, 2H), 4.20 (m, J=8 Hz, 1H), 2.87 (bm, 2H), 2.73 (hept, J=6Hz, 1H), 1.25 (d, J=6 Hz, 6H), 1.15 (d, J=8 Hz, 3H); MS(ESI)m/z 500 $(M+NH_4)^+$, 483$(M+H)^+$.

Step B. Isobutyric acid 3-(2-aminopropyl)-1H-indol-5-yl ester

Prepared from the product of Step A as described in Example 1, Step C: oil, 58% yield; $^1H$ NMR ($CDCl_3$) δ 8.2 (bs, 1H), 7.3 (d, J=8 Hz, 1H), 7.2 (s, 1H), 7.0(s, 1H), 6.85 (dd, J=8,2 Hz, 1H), 3.2 (m, 1H), 2.9–2.4 (m, 2H), 1.6 (m, 1H), 1.31 (d, J=6 Hz, 6H), 1.17 (d, J=8 Hz, 3H); MS(ESI) m/z 261 $(M+H)^+$.

EXAMPLE 3

2,2-Dimethyl-propionic acid 3-(2-aminopropyl)-1H-indol-5yl ester

Step A. 2,2-Dimethyl-propionic acid 3-[2(9H-fluoren-9-ylmethoxycarbonylamino)-propyl]-1H-indol-5-yl ester Prepared as described in Example 1, Step B but using pivaloyl chloride: oil, 49% yield; $^1$H NMR (CDCl$_3$) δ 8.05 (bs, 1H), 7.75 (d, J=6 Hz, 2H), 7.54 (d, J=6 Hz, 2H), 7.43–7.29 (m, 7H), 6.97 (bs, 1H), 6.87 (dd, J=8, 2 Hz, 1H), 4.43 (m, 1H), 4.37 (m, J=8 Hz, 2H), 4.20 (m, J=8 Hz, 1H), 2.87 (bm, 2H), 1.6 (s, 9H), 1.15 (d, J=8 Hz, 3H); MS(ESI) m/z 514 (M+NH$_4$)$^+$, 497 (M+H)$^+$.

Step B. 2,2-Dimethyl-propionic acid 3-(2-aminopropyl)-1H-indol-5-yl ester

Prepared from the product of Step A as described in Example 1, Step C: oil, 45% yield; $^1$H NMR (CDCl$_3$) δ 8.1 (bs, 1H), 7.3 (d, J=8 Hz, 1H), 7.2 (s, 1H), 7.0 (d, J=2.2 Hz, 1H), 6.85 (dd, J=8, 2 Hz, 1H), 3.2 (m, 1H), 2.8 (dd, J=14.2, 4.8 Hz, 1H), 2.62 (dd, J=14.2, 6.0 Hz, 1H), 1.39 (s, 9H), 1.17 (d, J=8 Hz, 3H); MS(ESI) m/z 275 (M+H)$^+$.

EXAMPLE 4

Cyclopropanecarboxylic acid 3-(2-aminopropyl)-1H-indol-5yl ester

Step A. Cyclopropanecarboxylic acid 3-[2-(9H-fluoren-9-ylmethoxycarbonylamino)propyl]-1H-indol-5-yl ester Prepared as described in Example 1, Step B but using cyclopropanecarbonyl chloride: oil, 57% yield; $^1$H NMR (CDCl$_3$) δ 8.05 (bs, 1H), 7.76 (d, J=6 Hz, 2H), 7.54 (d, J=6 Hz, 2H), 7.43–7.29 (m, 7H), 6.97 (bs, 1H), 6.87 (dd, J=8, 2 Hz, 1H), 4.7 (m, 1H), 4.4 (m, J=8 Hz, 2H), 4.20 (m, J=8 Hz, 1H), 4.0 (bs, 1H), 2.87 (bm, 2H), 1.8 (m, 1H), 1.7–1.1 (bm, 7H); MS(ESI) m/z 498 (M+NH$_4$)$^+$, 481 (M+H)$^+$.

Step B. Cyclopropanecarboxylic acid 3-(2-aminopropyl)-1H-indol5-yl ester

Prepared from the product of Step A as described in Example 1, Step C: oil, 62% yield; $^1$H NMR (CDCl$_3$) δ 8.1 (bs, 1H), 7.3 (d, J=8 Hz, 1H), 7.2 (s, 1H), 7.0 (s, 1H), 6.85 (dd, J=8,2 Hz, 1H), 3.2 (m, 1H), 2.8 (dd, J=14.2, 4.8 Hz, 1H), 2.62 (dd, J=14.2, 6.0 Hz, 1H), 1.9 (m, 1H), 1.2 (m, 4H), 1.17 (d, J=8 Hz, 3H); MS(ESI) m/z 259 (M+H)$^+$.

EXAMPLE 5

| Ingredients | Amount (wt %) |
|---|---|
| 2,2-Dimethyl-propionic acid 3-(2-aminopropyl)-1H-indol-5-yl ester | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 6

| Ingredients | Amount (wt %) |
|---|---|
| 2,2-Dimethyl-propionic acid 3-(2-aminopropyl)-1H-indol-5-yl ester | 0.01–2% |
| Methyl cellulose | 4.0% |
| Dibasic sodiumn phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 7

| Ingredients | Amount (wt %) |
|---|---|
| Cyclopropanecarboxylic acid 3-(2-aminopropyl)-1H-indol-5-yl ester | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 8

| Ingredients | Amount (wt %) |
|---|---|
| Cyclopropanecarboxylic acid 3-(2-aminopropyl)-1H-indol-5-yl ester | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |

EXAMPLE 9

Solution Stability Studies

The solution stability of the example compounds were assessed using an accelerated stress test. The compound was dissolved in pH 5, 0.025 M sodium citrate buffer (5~15 μg/mL). In duplicate, 2 mL of each solution in a glass vial was heated at 75° C. for 14 days. Samples were analyzed periodically using HPLC and % degradation was calculated for the sample. The predicted shelf life (25° C.) was based on the loss of 10% compound (T$_{90}$) and the fact that the rate of degradation for a first order reaction decreased 50% for every 10° C. drop in temperature.

TABLE 2

Compound Stability.

| Example | Predicted Shelf Life, months |
|---|---|
| α-methylserotonin | 2.6 |
| 1 | 1.32 |
| 2 | 3.36 |

TABLE 2-continued

Compound Stability.

| Example | Predicted Shelf Life, months |
|---------|------------------------------|
| 3 | 11.3 |
| 4 | 5.81 |

The predicted shelf lives for representative compounds of Formula I are listed in Table 2. The parent compound, α-methylserotonin, and the corresponding propionic acid ester derivative (Example 1) are included for reference. Example 1, a straight chain alkyl ester, did not provide an increase in the stability of the parent compound. The other Examples in Table 1, more sterically hindered esters, were less susceptible than the parent compound to both oxidative degradation and ester hydrolysis as illustrated by the decreased level of degradation observed under the experimental stress conditions.

What is claimed is:

1. A method for lowering and controlling normal or elevated intraocular pressure in a patient in need thereof which comprises administering a pharmaceutically effective amount of a compound of the formula:

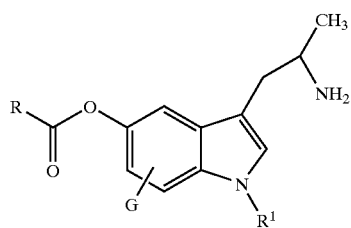

wherein G is chosen from hydrogen, halogen or $C_{1-4}$alkyl;

R is chosen from $C_{3-6}$alkyl, $C_{3-6}$alkyl substituted with hydroxyl, $CO(OC_{1-4}alkyl)$, $CON(C_{1-4}alkyl)_2$, or $C_{2-4}$alkenyl substituted by phenyl;

$R^1$ is chosen from hydrogen $C_{1-4}$alkyl;

and pharmaceutically acceptable salts and solvates.

2. The method of claim 1, wherein the compound is combined with one or more other agents selected from the group consisting of β-blockers, carbonic anhydrase inhibitors, $α_1$ antagonists, $α_2$ agonists, miotics, prostaglandin hypotensive lipids, and neuroprotectants.

3. The method of claim 2, wherein the one or more other agents are selected from the group consisting of timolol, betaxolol, levobetaxolol carteolol, levobunolol, propranolol, brinzolamide, dorzolamide, nipradolol iopidine, brimonidine, pilocarpine, epinephrine, latanoprost, travoprost, unoprostone, lumigan, eliprodil and R-eliprodil.

4. The method of claim 1, wherein the compound is selected from the group consisting of : isobutyric acid 3-(2-aminopropyl)-1H-indox-5-yl ester; 2,2dimethyl-propionic acid 3-(2-aminopropyl)-1H-indol-5-yl ester; and cyclopropanecarboxylic acid 3-(2-aminopropyl)-1H-indol-5-yl ester.

5. The method of claim 4, wherein the compound is 2,2dimethyl-propionic acid 3-(2-aminopropyl)-1H-indol-5yl ester.

* * * * *